United States Patent [19]

Munch

[11] Patent Number: 4,458,354
[45] Date of Patent: Jul. 3, 1984

[54] COUPLING DEVICE FOR COUPLING A RONTGEN TUBE-HOLDER TO THE FRAME OF AN IMAGE RECEIVER IN A TOMOGRAPH

[75] Inventor: Joseph Munch, Paris, France
[73] Assignee: Thomson-CSF, Paris, France
[21] Appl. No.: 385,290
[22] Filed: Jun. 4, 1982

[30] Foreign Application Priority Data
Jun. 10, 1981 [BE] Belgium ................................. 889156

[51] Int. Cl.³ .............................................. G03B 41/16
[52] U.S. Cl. ......................................... 378/25; 378/26
[58] Field of Search ...................... 378/21, 22, 25, 26, 378/23, 24, 27

[56] References Cited
U.S. PATENT DOCUMENTS
4,335,312  6/1982  Onken ..................................... 378/26

Primary Examiner—Alfred E. Smith
Assistant Examiner—T. N. Grigsby
Attorney, Agent, or Firm—Roland Plottel

[57] ABSTRACT

A coupling device for coupling a Röntgen tube-holder to the frame of an image receiver in a tomograph, namely a coupling device in which a coupling link is coupled between the frame of the image receiver and the Röntgen tube-holder for synchronously moving the image receiver and the Röntgen tube-holder, namely a coupling link one end of which is a non uncouplable coupling and the other end of which is an uncouplable coupling which is provided by a permanent electromagnetic coupling.

4 Claims, 3 Drawing Figures

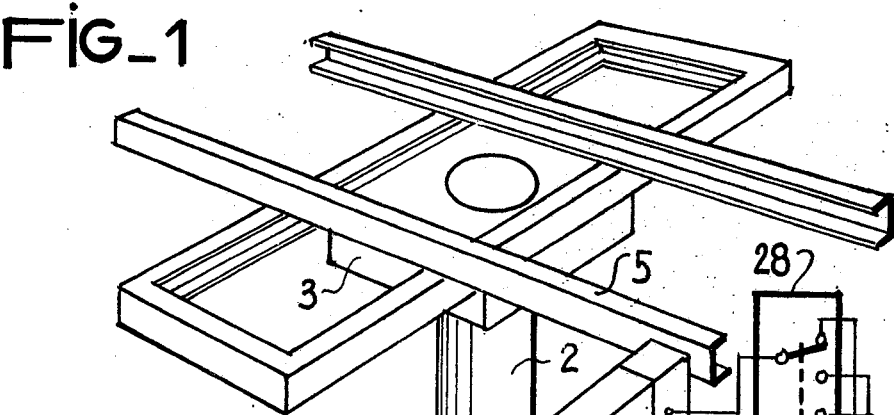
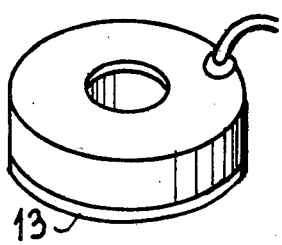
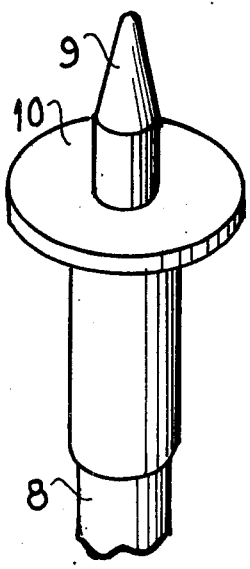
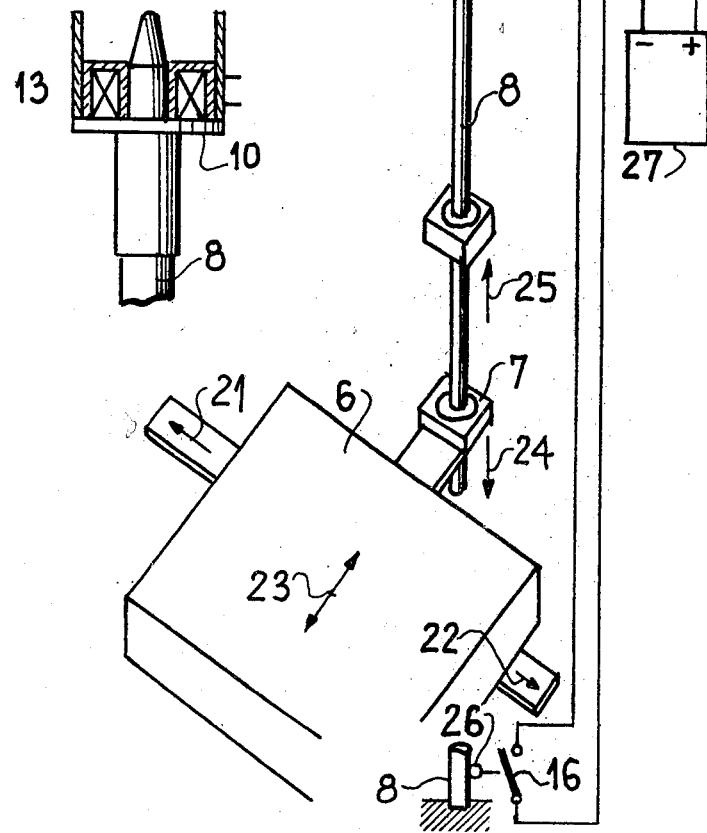

COUPLING DEVICE FOR COUPLING A RONTGEN TUBE-HOLDER TO THE FRAME OF AN IMAGE RECEIVER IN A TOMOGRAPH

BACKGROUND OF THE INVENTION

The invention relates to an uncouplable coupling device to be used for efficiently coupling the Röntgen tube-holder to the frame of an image receiver which is mounted lower down in a tomograph.

As is well known in specific radiological tomographs, the movable Röntgen tube-holder must be able to be coupled in a releasable way to the movable frame of the image receiver in a tomograph, so as to be able to obtain synchonous movement between the Röntgen tube-holder and the frame of the image receiver. Up to present, a coupling link has been used which, on the one hand, is fixed to the frame of the image receiver so as to function as a hinge and, on the other hand, is coupled releasably to the hinge of the Röntgen tube-holder. Further, the coupling link must be able to be uncoupled so as to allow free movement of the Röntgen tube-holder for other application techniques.

A known coupling device is for example the bayonet coupling device, namely a device in which a manual rotational movement is effected for connecting together the two parts of the coupling device, one part of which forms part of the Röntgen tube-holder and the other part of which is mounted at the upper part of the coupling link.

An important disadvantage of this coupling device resides in the fact that the operator of the tomograph must each time go to the back of the tomograph for coupling the coupling link to the Röntgen tube-holder or for uncoupling it therefrom and that, to do this, he must further effect a relatively complicated manoeuvre.

SUMMARY OF THE INVENTION

To obviate these drawbacks and in accordance with the main characteristic of the invention, the releasable coupling device of the invention is a permanent electromagnetic coupling. Thus, the operator of the tomograph may effect the coupling along the front face of the tomograph with a minimum of operations, while providing solid coupling between the frame of the image receiver and a Röntgen tube-holder.

BRIEF DESCRIPTION OF THE DRAWINGS

By way of example, there will be given hereafter a more detailed description, without any limiting character, of one chosen embodiment of the coupling in accordance with the invention. This description is accompanied by the drawings in which:

FIG. 1 is a perspective view of a part of the tomograph;

FIG. 2 is a perspective view of a coupling device in accordance with the invention; and FIG. 3 is a longitudinal section of this coupling device.

DESCRIPTION OF THE PREFERRED EMBODIMENT

In these figures it can be seen that the Röntgen tube-holder 1 of the tomograph is suspended from a telescope 2 and that the Röntgen tube-holder is thus adjustable in height. Telescope 2 is, in its turn suspended from a carriage 3 movable in a carriage 4 which is itself movable along rails 5 fixed to the ceiling, whereby the Röntgen tube-holder may move in all directions in a known way. Below the tomograph is mounted the movable frame 20, in the direction shown by the arrows 21, 22, 23, with the image receiver 6. To this frame 20 is coupled, by means of a non uncouplable spherical mass 7, a coupling link 8 axially movable in this mass in the directions shown by the arrows 24, 25. The upper end of this coupling link is equipped with a coupling pin 9 terminating in a point and with an abutment disk 10. On the arm 11 of the Röntgen tube-holder 1 there is fixed a case 12 mounted transversely pivotable on the longitudinal axis of this arm 11. In this case there is mounted a parmanent electro-magnet 13 having a central opening 14. The lower end 8A of the coupling link shown if low position, cooperates in this position with conventional means 26 to actuates a first switch 16.

When coupling link 8 is to be coupled to the Röntgen tube-holder 1, carriages 3,4 must be moved and telescope 2 shifted so that the permanent electro-magnet 13 is engaged by the coupling pin 9 and so that the abutment disk 10 is at rest against the permanent electro-magnet 13. By operating in off-position 0 a second switch 15 mounted on the tomograph during coupling link 8 is moved up, the permanent electro-magnet 13 is energized by D.C. current having such polarities that the coupling pin 9 is attracted by the permanent electro-magnet 13 to which it is solidly fixed. This D.C. current, applied to permanent electro-magnet 13 trough a relay 28, is provided from a power supply 27. The said relay 28 is actuated by first switch 16 provided that the second switch 15 is not in off-position 0 an util end 8A is drawn up enough. Because the coupling device is a permanent electro-magnet coupling, the coupling pin 9 will remain coupled to the electro-magnet 13, even should there occur a current failure, because of the permanent magnetic coupling force. For uncoupling the coupling, the coupling link 8 is placed in the vertical position by moving carriages 3 and 4. Then telescope 2 is drawn downwards, whereby the coupling link 8, also moved downwards with the telescope, actuates switch 16 mounted below and which changes automatically the polarities in the permanent electro-magnet 13. Thus, the coupling link 8 in uncoupled while remaining in its lowest position. The operator of the apparatus pushes telescope 2 upwards so that the coupling is completely broken.

It goes without saying that the form and dimensions of the above-described coupling, as well as the mounting of the parts thereof in their respective positions, may differ provided that they remain within the scope of the invention.

What is claimed is:

1. In a coupling for coupling the Röntgen tube-holder to the image receiver in a tomograph, namely a coupling link coupled between the frame of the image receiver and the Röntgen tube-holder for synchronously moving the image receiver and the Röntgen tube-holder, one end of said coupling link having one non uncouplable end and the other end having an uncouplable coupling, said uncouplable coupling is a permanent electromagnetic coupling, wherein said permanent electromagnetic coupling comprises a coupling pin placed at the upper end of the coupling link and a permanent electromagnet placed in a case which may pivot with respect to the Röntgen tube-holder and wherein the coupling pin in the coupled position is pushed into the central hole of said permanent electromagnet and is held there.

2. The coupling as claimed in claim 1, wherein said coupling pin ends in a point.

3. The coupling as claimed in claim 1, wherein said coupling pin is provided with an abutment disk which, in the coupled position of said coupling pin, is right against the electromagnet which forms the other part of the coupling.

4. The coupling as claimed in claim 1, wherein means are provided for cooperating with said coupling link in its lowest and vertical position for controlling the permanent electromagnet coupling and the uncoupling of the coupling.

* * * * *